March 21, 1933. J. H. DICKEY Plant Pat. 57
APPLE TREE
Filed May 23, 1932
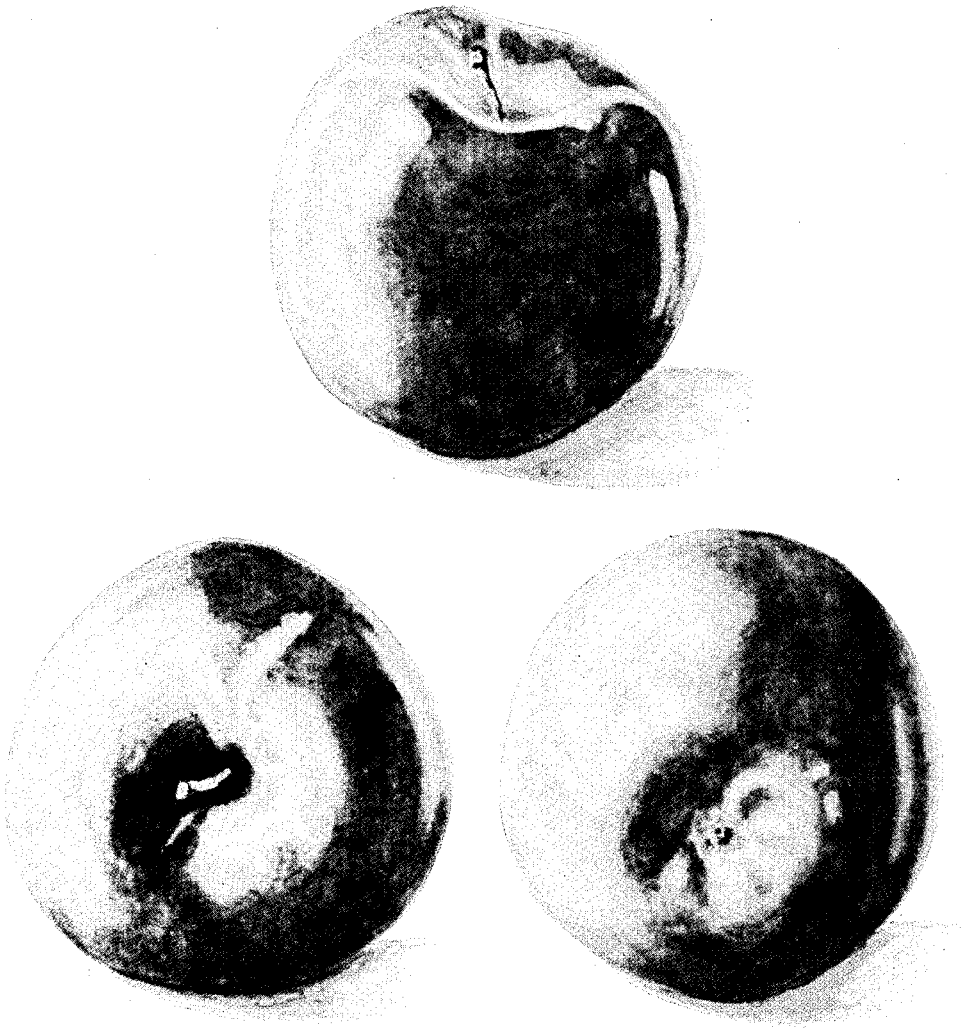
Inventor
J. H. Dickey
By Robb & Robb
Attorneys Patented Mar. 21, 1933

UNITED STATES PATENT OFFICE

JOHN H. DICKEY, OF WENATCHEE, WASHINGTON, ASSIGNOR TO STARK BRO'S NURSERIES & ORCHARDS COMPANY, OF LOUISIANA, MISSOURI

APPLE TREE

Application filed May 23, 1932. Serial No. 613,053.

This discovery relates to a new and distinct variety of apple tree which was originally discovered as a limb sport upon a Stayman winesap tree, indicating a very notable variation therefrom in that the apples on the limb colored all over a brilliant and solid red approximately thirty days before the apples on the rest of the tree were ripe.

It is quite well known that a red colored apple is in much greater demand by the public for several reasons; first, because there is greater attractiveness in the red color; and second, red colored apples have a longer keeping quality and do not scald.

This difference in color, therefore, represents a difference in marketability, commercial demand and price or profit.

It is also a well known fact that in many sections, the regular Stayman winesap colors very poorly and in fact a very small percentage only gets into the extra fancy color.

As distinguished from this, the present bud sport apple becomes a bright red color all over, which fact eliminates the loss in price due to poorly colored fruit, and thus puts a much larger percentage into the extra fancy high priced grades, which bring greatly increased profits to the grower as compared to the old standard Stayman winesap, which frequently goes largely to the lower priced, poorly colored grades.

Early coloring has several advantages:—It means that the grower does not have to leave the fruit on the tree until it is over-ripe in an endeavor to get more color and thus get into the higher extra fancy grades which bring the most profit. By being able to pick the fruit when it is hard ripe and yet has plenty of color, as is the case of this new bud sport, the fruit will retain its solidity and keeping quality much longer. The higher color makes it much more attractive and it sells at a higher price than poorer colored or regular Stayman winesap apples. The higher colored fruit does not scald as does the poorer colored regular Stayman winesap fruit.

It is to be understood that while this new variety colors red about thirty days before the Stayman winesap grown under comparable conditions or on the same tree, it does not ripen any earlier than the said winesap.

The distinction in this new variety resides dominantly in the early coloring characteristic of the fruit, but a detail technical description is given as follows:

*Size.*—Medium to large; *form*—conical to oblate-conic. Unsymmetrical, nearly regular in cross-section. *Stem*—medium length and thickness, brown, pubescent. *Base*—board. *Cavity*—wide, deep, acute, pubescent, with thin brown russeting extending nearly over the entire cavity. *Apex*—medium width; *basin*—rather narrow, shallow, obscurely 5-furrowed. *Calyx*—small, closed; *lobes*—green, convergent, pubescent.

*Surface.*—Smooth, glossy, waxy, almost oily. No scarfskin. Dots numerous, a very few russet and prominent, others submerged, yellowish or pink, inconspicuous. *Color.*—Range from the *amber yellow of the undercolor visible only on the shaded portions of the fruit, through *peach red, *nopal red to *carmine. These colors are given as approximately as possible and are not to be taken as exact in relation to fruit colors. The general effect is bright crimson.

*Flesh color.*—White with faint greenish yellow tinge. *Veins.*—Scarcely outlined yellowish green. *Carpels.*—Obovate, *light dull green yellow. *Seeds.*—Large *mahogany red. *Flesh texture.*—Rather firm, a little coarse and spongy, slight fiber, juicy. *Flavor.*—Mild subacid, pleasing aroma. *Quality.*—Very good.

What I claim as new is:

A new and distinct variety of apple tree as described, characterized by the early coloring brilliant red of its fruit before ripening, as herein shown.

In testimony whereof I affix my signature.

JOHN H. DICKEY.

* Ridgeway's Color Standard.